US008647830B2

(12) United States Patent
Bergmann et al.

(10) Patent No.: US 8,647,830 B2
(45) Date of Patent: Feb. 11, 2014

(54) METHOD FOR DETERMINING AMINO-TERMINAL PROANP IN PATIENTS HAVING A CARDIAC DISEASE OR BEING SUSPECTED OF DEVELOPING OR HAVING A CARDIAC DISEASE (75) Inventors: Andreas Bergmann, Berlin (DE); Jana Papassotiriou, Berlin (DE); Joachim Struck, Berlin (DE); Nils Morgenthaler, Berlin (DE); Stefan Anker, Berlin (DE)

(73) Assignee: B.R.A.H.M.S. GmbH, Henningsdorf (DE)

( * ) Notice: Subject to any disclaimer, the term of this patent is extended or adjusted under 35 U.S.C. 154(b) by 783 days.

(21) Appl. No.: 12/598,982

(22) PCT Filed: May 6, 2008

(86) PCT No.: PCT/EP2008/055535
§ 371 (c)(1),
(2), (4) Date: Jul. 20, 2010

(87) PCT Pub. No.: WO2008/135571
PCT Pub. Date: Nov. 13, 2008

(65) Prior Publication Data
US 2010/0285493 A1 Nov. 11, 2010

(30) Foreign Application Priority Data
May 7, 2007 (DE) .......................... 10 2007 022 367

(51) Int. Cl.
*G01N 33/53* (2006.01)
*G01N 31/00* (2006.01)

(52) U.S. Cl.
USPC ............ 435/7.21; 435/7.1; 436/86; 436/501; 436/518; 514/23; 514/80; 514/454; 514/532; 530/300; 530/350

(58) Field of Classification Search
None
See application file for complete search history.

(56) References Cited

U.S. PATENT DOCUMENTS

| 7,361,473 | B2 | 4/2008 | Valkirs et al. |
| 2006/0234295 | A1 | 10/2006 | Bergmann et al. |
| 2010/0173321 | A1 | 7/2010 | Hamm et al. |

FOREIGN PATENT DOCUMENTS

| EP | 1731910 A1 | 12/2006 |
| JP | 2004-037455 | 2/2004 |
| JP | 2006-523298 | 10/2006 |
| WO | 0019207 A2 | 4/2000 |
| WO | WO 2004/046181 | 6/2004 |
| WO | 2006087373 A1 | 8/2006 |
| WO | WO 2006/131529 | 12/2006 |
| WO | PCTEP0855535 R | 10/2008 |
| WO | WO 2008/135571 | 11/2008 |

OTHER PUBLICATIONS

Missbichler et al. (European Journal of Medical Research, Mar. 26, 2001, pp. 105-111).*
Morgenthaler et al. (Clinical Chemistry, 2004, vol. 50, No. 1, pp. 234-236).*
Richards et al. (Circulation, 1998, vol. 97, pp. 1921-1929).*
Krauser et al. (American Heart Journal, Apr. 2005, vol. 149, No. 4, pp. 744-750).*
Richards, A. M., et al., "Plasma N-Terminal Pro-Brain Natriuretic Peptide and Adrenomedullin: New Neurohormonal Predictors of Left Ventricular Function and Prognosis After Myocardial Infarction," Circulation—Journal of the American Heart Association, 1998; 97; 1921-1929—Downloaded from circ.ahajournals.org on Jan. 19, 2010.
Qi, Y. F., et al., "Effects of Different Peptide Fragments Derived from Proadrenomedullin on Gene Expression of Adrenomedullin Gene," Peptides 23 (2002) 1141-1147.
Missbichler, A. et al. "Sandwich Elisa for proANP 1-98 Facilitates Investigation of Left Ventricular Dysfunction." (European Journal of Medical Research), Mar. 26, 2001, 105-111, 6:3.
Galasko, Gavin et al. "Comparison of the clinical utility of atrial and B type natriuretic peptide measurement for the diagnosis of systolic dysfunction in a low-risk population." (Journal of Clinical Pathology), May 2007, 570-572, 60:5.
Rubattu, Speranza et al. "Reduced levels of N-terminal-proatrial natriuretic peptide in hypertensive patients with metabolic syndrome and their relationship with left ventricular mass." (Journal of Hypertension), Apr. 2007, 833-839, 25:4.
"Metabolic syndrome" [Wikipedia Online] XP002495698, Retrieved from the Internet: URL: http://en.wikipedia.org/w/index.php?title=Metabolic_syndrome&printable=yes> [retrieved on Sep. 11, 2008].

(Continued)

*Primary Examiner* — Lisa Cook
(74) *Attorney, Agent, or Firm* — Millen, White, Zelano, Branigan, P.C.

(57) ABSTRACT

The present invention relates to an in vitro method for medical diagnosis, prognosis and therapy follow-up for patients having a cardiac disease or being suspected of developing or having a cardiac disease comprising the steps of: providing a sample of a patient having a cardiac disease or being suspected of developing or having a cardiac disease, determining amino-terminal proANp or partial peptides thereof having from 12 to 98 amino acids in said sample using at least one antibody that binds specifically to a partial sequence of amino-terminal proANP, attributing the determined amino-terminal proANP level or the level of partial peptides thereof to a clinical picture wherein the attribution is carried out independent of the BMI of the patient. The present invention further concerns a rapid test assay and a kit for conducting the method of the present invention and the use of antibodies suitable for the method and assays according to the present invention.

19 Claims, 9 Drawing Sheets (56) References Cited

OTHER PUBLICATIONS

Tzikas et al., "Midregional pro-atrial natriuretic peptide in the general population", Clin. Chem. Lab. Med. Nov. 23, 2012, 109. (Abstract).

Chandler et al., "The place of gold in rapid tests", IVD Technology, Mar. 1, 2000, pp. 1-4.

English Translation of Chinese Office Action in Chinese Appln. No. 2008/80015355.0, corresponding to PCT/EP2008/055535, dated Jul. 5, 2012.

English Translation of Chinese Office Action in Chinese Appln. No. 2008/80015355.0, corresponding to PCT/EP2008/055535, dated Mar. 13, 2013.

European Examination Report in European Appln. No. 08 750 087.2 dated Apr. 26, 2011.

European Examination Report in European Appln No. 08 750 087.2, dated Oct. 8, 2012.

Indian Examination Report in Indian Appln. No. 1923/MUMNP/2009, corresponding to PCT/EP2008/055535, dated Apr. 10, 2013.

Translation of Japanese Office Action in Japanese Appln. No. 2010-506917, corresponding to PCT/EP2008/055535, dated Apr. 24, 2012.

Translation of Japanese Office Action in Japanese Appln. No. 2010-506917, corresponding to PCT/EP2008/055535, dated Mar. 12, 2013.

* cited by examiner

Fig. 1:

```
Asn Pro Met Tyr Asn Ala Val Ser Asn Ala Asp Leu Met Asp Phe Lys
1               5               10                  15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
            35                  40                  45

Leu Ser Pro Leu Pro Glu Val Pro Pro Trp Thr Gly Glu Val Ser Pro
        50              55                  60

Ala Gln Arg Asp Gly Gly Ala Leu Gly Arg Gly Pro Trp Asp Ser Ser
65              70                  75                      80

Asp Arg Ser Ala Leu Leu Lys Ser Lys Leu Arg Ala Leu Leu Thr Ala
                85                  90                  95

Pro Arg
```

Fig. 2:

| | | | | | | | | | | | | | |
|---|---|---|---|---|---|---|---|---|---|---|---|---|---|
|Asn|Pro|Met|Tyr|Asn|Ala|Val|Ser|Asn|Ala|Asp|Leu|Met|Asp|Phe|Lys
1| | | |5| | | | |10| | | | |15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
            35                  40                  45

Leu Ser Pro Leu Pro Glu Val Pro Pro Trp Thr Gly Glu Val Ser Pro
        50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg Ser Leu Arg Arg Ser Ser Cys Phe Gly Gly Arg Met Asp Arg
            100                 105                 110

Ile Gly Ala Gln Ser Gly Leu Gly Cys Asn Ser Phe Arg Tyr Arg Arg
        115                 120

Table 2. Logistic regression analysis for prediction of heart failure by MR-proANP and NT-proBNP

| Analyte | Optimal cut-off concentration | Odds ratio (95% CI) | p | Diagnostic accuracy, % | False-positive, n | False-negative, n |
|---|---|---|---|---|---|---|
| *Unadjusted model* | | | | | | |
| MR-proANP (pmol/l) | 206 | 26 (14-50) | <0.001 | 84 | 22 | 25 |
| NT-proBNP (pg/ml) | 1540 | 30 (16-56) | <0.001 | 85 | 21 | 23 |
| *Adjusted model\** | | | | | | |
| MR-proANP (pmol/l) | 206 | 20 (9-45) | <0.001 | 83 | 25 | 23 |
| NT-proBNP (pg/ml) | 1540 | 19 (9-42) | <0.001 | 83 | 24 | 23 |

* Adjusted for age, history of heart failure, prior myocardial infarction, glomerular filtration rate, hemoglobin, pulmonary rales, peripheral edema, jugular venous distension

SEQUENCE LISTING

<160> NUMBER OF SEQ ID NOS: 2

<210> SEQ ID NO 1
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
        35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg

```
<210> SEQ ID NO 2
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp Glu Val
            20                  25                  30

Val Pro Pro Gln Val Leu Ser Glu Pro Asn Glu Glu Ala Gly Ala Ala
        35                  40                  45

Leu Ser Pro Leu Pro Glu Val Pro Pro Trp Thr Gly Glu Val Ser Pro
    50                  55                  60

Ala Gln Arg Asp Gly Gly Ala Leu Gly Arg Gly Pro Trp Asp Ser Ser
65                  70                  75                  80

Asp Arg Ser Ala Leu Leu Lys Ser Lys Leu Arg Ala Leu Leu Thr Ala
                85                  90                  95

Pro Arg Ser Leu Arg Arg Ser Ser Cys Phe Gly Gly Arg Met Asp Arg
            100                 105                 110

Ile Gly Ala Gln Ser Gly Leu Gly Cys Asn Ser Phe Arg Tyr Arg Arg
            115                 120                 125
```

METHOD FOR DETERMINING AMINO-TERMINAL PROANP IN PATIENTS HAVING A CARDIAC DISEASE OR BEING SUSPECTED OF DEVELOPING OR HAVING A CARDIAC DISEASE

BACKGROUND OF THE INVENTION

This application is a continuation 371 of PCT/EP08/55535 filed May 6, 2008 which claims priority to German 10 2007 022 3678, filed May 7, 2007.

The present invention concerns an in vitro method for medical diagnosis, prognosis and therapy follow-up for patients having a cardiac disease or being suspected of developing or having a cardiac disease comprising the steps of:
- providing a sample of a patient having a cardiac disease or being suspected of developing or having a cardiac disease,
- determining amino-terminal proANP or partial peptides thereof having from 12 to 98 amino acids in said sample using at least one antibody that binds specifically to a partial sequence of amino-terminal proANP,
- attributing the determined amino-terminal proANP level or the level of partial peptides thereof to a clinical picture wherein the attribution is carried out independent of the BMI of the patient.

The present invention further concerns a rapid test assay for conducting the method of the present invention and the use of antibodies suitable for the method and assays according to the present invention.

Heart failure (HF) is common, associated with high morbidity and mortality, and difficult to diagnose, particularly in the emergency department (ED) [Cleland, J. G. et al., Eur Heart J, 2003. 24(5): p. 442-63; Mosterd, A. et al., Heart, 2007. 93(9): p. 1137-46]. Dyspnea is the leading symptom of most HF patients. Unfortunately, neither patient history nor physical examination can accurately differentiate dyspnea due to HF from dyspnea due to other causes, such as pulmonary diseases [Mueller, C. et al., Can J Cardiol, 2005. 21(11): p. 921-4; Wang, C. S. et al., Jama, 2005. 294(15): p. 1944-56]. However, accurate diagnosis is mandatory for the selection of the most appropriate treatment.

B-type natriuretic peptides are quantitative markers of HF that have been shown to be very helpful in the diagnosis of HF. The use of B-type natriuretic peptide (BNP) and its amino-terminal fragment, N-terminal pro-B-type natriuretic peptide (NT-proBNP) significantly increases the diagnostic accuracy in the ED [Januzzi, J. L., Jr., et al., Am J Cardiol, 2005. 95(8): p. 948-54; Maisel, A. S. et al., N Engl J Med, 2002. 347(3): p. 161-7], and thereby improves patient evaluation and treatment [Moe, G. W. et al., Circulation, 2007. 115(24): p. 3103-10; Mueller, C. et al., N Engl J Med, 2004. 350(7): p. 647-54].

The concentration of atrial natriuretic peptide (ANP) in the circulation is approximately 50- to 100- fold higher than BNP [Pandey, K. N., Peptides, 2005. 26(6): p. 901-32.]. Therefore, the biological signal reflected by the increased ANP may be pathophysiologically and therefore diagnostically even more important than the signal of BNP. Despite this, little is known about the diagnostic performance of ANP and its precursors [Cowie, M. R. et al., Lancet, 1997. 350(9088): p. 1349-53]. Mature ANP is derived from the precursor N-terminal-proANP(NT-proANP), which is significantly more stable in the circulation than the mature peptide and is therefore thought to be a more reliable analyte [Vesely, D. L., IUBMB Life, 2002. 53(3): p. 153-9]. Nevertheless, due to the fact that NT-proANP might be subject to further fragmentation [Cappellin, E. et al., Clin Chim Acta, 2001. 310(1): p. 49-52], immunoassays for measurement of mid-regional proANP (MR-proANP) may have an advantage [Morgenthaler, N. G. et al., Clin Chem, 2004. 50(1): p. 234-6].

Cardiac diseases, such as chronic heart failure (CHF), acute heart failure, acute coronary syndrome and myocardial infarction are widely spread and often have a devastating prognosis. Early prognosis of the cardiac disease can improve patient outcome through timely preventive and therapeutic measures [Jortani, S. A. et al., Clin Chem 2004; 50:265-278]. A wealth of data suggest that the assessment of natriuretic peptides represents a useful addition to chest X-ray, electrocardiogram, and doppler echocardigraphy in verifying the clinical diagnosis and prognosis for suspected cardiac diseases [Cowie, M. R. et al., Eur Heart J 2003; 24:1710-1718]. The most important members of the family of natriuretic peptides are atrial natriuretic peptide (ANP) and B-type natriuretic peptide (BNP). Both are markers of cardiac function. In addition to the use in helping to establish the diagnosis of CHF [Cowie, M. R. et al., Lancet, 1997. 350(9088): p. 1349-53; Mueller, C. et al., N Engl J Med, 2004. 350(7): p. 647-54], they are used in the risk stratification of patients with stable or recently decompensated CHF [Omland, T. et al., Cirulation 1996; 93:1963-1969; Anand, I. S. et al., Circulation 2003; 107:1278-1283; Cheng, V. et al, J Am Coll Cardiol 2001; 37:386-391], or with acute coronary syndrome [Morrow, D. A. et al., JAMA 2005, December 14; 294(22):2866-71] and, in addition, are used in follow-up and guidance in CHF therapy [Troughton, R. W. et al., Lancet 2000, 355:1126-1130].

Both BNP and the other cleavage product of its precursor, N-terminal proBNP(NT-proBNP) are currently used in the assessment of patients with CHF. ANP originates from the cleavage of its precursor proANP. The other cleavage product, N-terminal proANP (NT-proANP) is significantly more stable in circulation than ANP. Therefore, NT-proANP has been suggested to be a more reliable analyte in the prior art [Ala-Kopsala, M. et al., Clin Chem, 2004. 50(9): p. 1576-88]. However, the N- and C-terminal regions of the N-terminal pro-peptide can be altered through enzymatic degradation [Seidler, T. et al., Biochem Biophys Res Commun 1999, 255:495-501]. Commonly, BNP and NT-proBNP are considered as being more suitable for the diagnosis and prognosis in patients with cardiac insufficiency than ANP and NT-proANP. The reason for this may be that the determination of ANP and NT-proANP is considered less reproducible, and that conceptual flaws in most of the applied assay designs lead to a partial underestimation of the amount of circulating analyte [Yoshibayashi, M. et al., Eur J. Endocrinol 1996; 135:265-268; Vesely, D. L. et al., IUBMB Life, 2002. 53(3): p. 153-9].

Usually, a peptide comprising 28 amino acids (99-126) of the C-terminal section of a pro-hormone comprising 128 amino acids (proANP; SEQ ID NO: 2) is referred to as the actual hormone ANP. Upon release of ANP from its pro-hormone proANP, an equimolar amount of the remaining larger partial peptide of proANP, the N-terminal proANP, consisting of 98 amino acids (NT-proANP; proANP (1-98)) is released into circulation. As NT-proANP possesses a significantly greater half life time and stability NT-proANP can be used as laboratory parameter for diagnosis, follow-up and therapy control in cardiac diseases. For a deeper insight into the topic please refer to: Lothar Thomas (Editor), Labor and Diagnose, 5th expanded ed., sub-chapter 2.14 of chapter 2, Kardiale Diagnostik, pages 116-118, and the literature cited therein.

Both for the determination of ANP itself as well as for the determination of NT-proANP in biological liquids (serum, plasma, urine), various immunoassays have been developed in the past and have been applied in clinical research and practice. The major part of such immunoassays for the determination of ANP and NT-proANP is based on the known principle of competitive immunoassays, the best known of which is the radioimmunoassay (RIA). Competitive immunoassays for the determination of proANP and ANP are described or used, for instance in [Cappellin, E. et al., Clin Chim Acta, 2001. 310(1): p. 49-52] and [Hiroshi Itoh et al., Journal of Hypertension 1988, 6 (suppl 4) S309-S319; Meleagros, L. et al., Peptides, Vol. 10, 545-550, 1989; Amir Lerman et al., Lancet 1993, 341:1105-09, 1993; John G F Cleland et al., Heart 1996, 75:410-413; Martin G. Buckley et al., Clinical Science (1999) 97:689-695].

By the use of various antibodies which recognize various sequences of NT-proANP (NT-proANP 1-98; SEQ ID NO: 1) for the determination of NT-proANP with competitive immunoassays, it was interpreted that various peptides appear in biological liquids, in particular blood or urine, which correspond to degradation products of NT-proANP (proANP 1-98). In particular, it has been interpreted that low molecular fragments are formed form NT-proANP, in particular such fragments, to which the amino acid sequences 1-30, 31-67 and 79-98 of proANP have been addressed due to their immunoactivity (cf. e.g. M. G. Buckley et al., Clinica Chimica Acta, 191 (1990) 1-14; J. B. Hansen et al., Lab. Invest. 1995, 55:447-452; Rose M. Overton et al., Human Plasma and Serum; Peptides, Vol. 17, 1155-1162, 1996; Sreedevi Daggubati et al., Cardiovascular Research 36 (1997) 246-255; E. F. Macaulay Hunter et al., Scand J Clin Invest 1998; 58: 205-216; Martina Franz et al., Kidney International, Vol. 58 (2000), 374-383, Fumiaki Marumo et al., Human Plasma and Urine; Biochem. Biophys. Res. Commun. 137:231-236 (1985) and Engelbert Hartter et al., Clin Chem Lab Med 2000, 38(19): 27-32).

Competitive immunoassays which specifically recognize the above-mentioned sequences always recognize the full NT-proANP in the same manner—disregarding influences based on different avidities or possible conformational influences—and do therefore not differentiate between NT-proANP and its fragments.

In contrast to competitive immunoassays, non-competitive sandwich immunoassays show a number of advantages. For instance, they can be interpreted as solid phase assays (heterogeneous assays) more readily, are more robust, provide measurement results with a greater sensitivity, exhibit less cross-reactivity, and are more suitable for automation and serial measurements. Furthermore, by recognizing only such molecules and/or peptides in which both binding moieties for the antibodies which are used for the sandwich formation are present in the same molecule, sandwich immunoassays may lead to slightly different conclusions in comparison with competitive immunoassays which only apply one type of antibody. If, for instance, the binding areas are located on different partial peptides (degradation product, fragments) a binding of the antibodies to such fragments will not lead to the measurement signal which is typical for the complete "sandwich".

Due to the known advantages of sandwich immunoassays in principle as well as due to the possibility of selectively measuring only complete NT-proANP without any influence of degradation products and fragments, sandwich immunoassays for the determination of NT-proANP have already been described and applied in clinical research and practice. For instance, EP 721 105 B1 describes a sandwich immunoassay for the determination of proANP, in particular in the area of diagnosis of cardiac diseases and chronic kidney failure, to using two monoclonal antibodies, one of which binds to amino acids 1-25 of proANP (compare EP 350 218 B1) and the other of which binds to amino acids 43-66 of proANP. By this kind of sandwich immunoassay, only such proANP partial peptides are detected or co-detected in the presence of proANP (1-98), which comprise at least the first 66 amino acids of the proANP sequence.

Another sandwich immunoassay which is similar in this respect is described in [Mats Stridsberg et al., J. Med. Sci 102, 99-108, Vol. 18: 1201-1203]. This sandwich immunoassay also uses two monoclonal antibodies, one of which binds to amino acids 1-30 of proANP, while the other binds to amino acids 79-98. Due to the choice of binding areas at the terminal ends of proANP (1-98) it can be assumed that this sandwich immunoassay will only detect intact proANP (1-98).

WO 00/19207 describes a method for the determination of proANP (1-98) in which two of three polyclonal antibodies are used, which bind to the amino acid sequences 8-27, 31-64 or 79-98 of the proANP (1-98) sequence. The assay for the determination of proANP (1-98) commercially offered by the applicant of WO 00/19207 is an enzyme immunoassay, using a pair of affinity purified polyclonal sheep antibodies, of which the immobilized antibody recognizes amino acids 10-19 of proANP, while a second polyclonal antibody is used for detection, which recognizes amino acids (85-90) (compare operation manual of the sandwich assay proANP (1-98) by BIOMEDICA, A-1210 Wien). Thus, this assay also recognizes only peptide species containing the terminal ends of the full proANP (1-98), i.e. complete or nearly complete NT-proANP).

All competitive assays or assays which apply the sandwich principle described in the prior art have basically been developed as assays for cardiac diagnostics or which have been used in the context of cardiac diagnostics, whereby chronic kidney failure has been mentioned as further diagnostic application (compare EP 721 105 B1 and citation [Buckley M G et al., AM. J. Hypertens. 1990 December, 3 (12 Pt 1): 933-935]).

Furthermore, a new sandwich immunoassay for the determination of the central region of proANP (amino acids 53-73) has been developed, the measurement results of which are not influenced by a putative terminal truncation of the peptide [Clinical Chemistry 50, No. 1, 2004, pages 234-236].

It was an object of the invention to provide an in vitro method for medical diagnosis, prognosis and therapy follow-up for patients having a cardiac disease or being suspected of developing or having a cardiac disease which provides reliable information especially to the medical practitioner in the Emergency Department (ED).

Thus, the present invention comprises an in vitro method for medical diagnosis, prognosis and therapy follow-up for patients having a cardiac disease or being suspected of developing or having a cardiac disease comprising the steps of:
  providing a sample of a patient having a cardiac disease or being suspected of developing or having a cardiac disease,
  determining amino-terminal proANP or partial peptides thereof having from 12 to 98 amino acids in said sample using at least one antibody that binds specifically to a partial sequence of amino-terminal proANP,
  attributing the determined amino-terminal proANP level or the level of partial peptides thereof to a clinical picture wherein the attribution is carried out independent of the BMI of the patient.

Preferably, the in vitro method according to the present invention is carried out, wherein the attribution to a clinical picture is carried out with help of a BMI independent cut-off value.

Attribution to a clinical picture means that the determined amino-terminal proANP level or the level of partial peptides thereof is used for the medical diagnosis, prognosis or therapy follow-up for patients having a cardiac disease or being suspected of developing or having a cardiac disease wherein the use is carried out independent of the BMI of the patient.

The cardiac disease of the patient may be selected from but not restricted to chronic heart failure, acute heart failure, acute coronary syndrome or myocardial infarction.

In one embodiment of the invention the disease is diagnosed, thus said method is a method for medical diagnosis.

In one preferred embodiment of the invention the cardiac disease is heart failure. The in vitro method according to the invention is especially well-suited and reliable for patients that exhibit symptoms of dyspnea and are therefore suspected of having heart failure and the clinical picture is diagnosed. The evaluation and management of patients presenting to the Emergency Department is facilitated by the method according to the present invention. Accurate diagnosis is mandatory for the selection of the most appropriate treatment for such patients. Therefore, the present invention meets the need to accurately differentiate dyspnea due to heart failure from dyspnea due to other causes, such as pulmonary diseases. The method according to the present invention, therefore, significantly improves diagnostic accuracy for heart failure.

BRIEF DESCRIPTION OF THE DRAWINGS

NT-proBNP=N-terminal pro-B-type natriuretic peptide; MR-proANP=midregional pro-atrial natriuretic peptide.

Boxes represent the $25^{th}$ and $75^{th}$ percentile, whereas whiskers represent the minimum to the maximum concentration, excluding outliers which are displayed as separate points.

DETAILED DESCRIPTION OF THE INVENTION

It has been described that the concentration of NT-proANP as well as of BNP is reduced with increasing BMI in the healthy population [Wang, T. J. et al., Circulation, 2004. 109(5): p. 594-600]. The authors therefore deduce that natriuretic peptides rather are not suitable as markers in obese patients ("Second, plasma natriuretic peptide levels may be a less useful marker for heart failure or left ventricular dysfunction in obese individuals, a speculation that merits investigation.").

Surprisingly, it has been found in the context of this invention that for a certain sub-population of patients with a cardiac disease (chronic heart failure), namely such with a BMI (Body Mass Index) of equal or greater than 30 kg/cm$^2$, in particular the determination of amino terminal proANP or partial peptides derived thereof in a biological sample originating from these patients allows for a reliable prognosis. This is exactly the sub-population, of which Wang, et al. deduced that natriuretic peptides may be less useful markers. It has been described in a recent publication that BNP also has a prognostic value in the sub-group of obese patients in hospitalized patients which chronic heart failure [Horwich, T. B. et al., J. Am. Coll. Cardiol. 2006, Jan. 3, 47(1):85-90; Epub 2005, December 15]. In the context of this invention, it has been found surprisingly that NT-proANP has been more reliable in respect to the prognosis of said sub-population of patients in comparison with the BNP analogue NT-proBNP.

In the following a preferred embodiment of the present invention is described relating to a in vitro method, wherein the patient or the patient group has a BMI of equal or greater than 30 kg/m$^2$ and the sample is provided by a patient having a BMI of equal or greater than 30 kg/m$^2$.

A subject of the present invention is an in vitro method according to the present invention, wherein the patient or the patient group has a BMI of equal or greater than 30 kg/m$^2$ and the sample is provided by a patient having a BMI of equal or greater than 30 kg/m$^2$.

Thus, a subject of the present invention is an in vitro method for medical diagnosis, prognosis and therapy follow-up for patients having a cardiac disease or being suspected of developing or having a cardiac disease and having a BMI of equal or greater than 30 kg/m$^2$, comprising the following steps:
  providing a sample of a patient having a cardiac disease or being suspected of developing or having a cardiac disease and a BMI of equal or greater than 30 kg/m$^2$, and
  determining amino-terminal proANP or partial peptides thereof in said sample using at least one antibody that binds specifically to partial sequences of amino-terminal proANP.

The method according to the present invention is particularly suitable for the diagnosis, prognosis and therapy follow-up in patients having chronic heart failure.

The method according to the present invention is particularly suitable for the diagnosis, prognosis and therapy follow-up in patients having chronic heart failure and having a BMI of equal or greater than 30 kg/m$^2$. The method according to the present invention is especially well suited for the prognosis for patients having a cardiac disease or being suspected of developing or having a cardiac disease and having a BMI of equal or greater than 30 kg/m$^2$, especially in case wherein the disease is chronic heart failure.

In this patient group, i.e. patients having a cardiac disease or being suspected of developing or having a cardiac disease and having a BMI of equal or greater than 30 kg/m², especially in case wherein the disease is chronic heart failure, the method according to the invention is preferably carried out on patients who are not (supposedly) asymptomatic.

In a particularly preferred embodiment the optimum threshold for the mortality prognosis in the patient group with a BMI equal or greater than 30 kg/m² is in the range between 190 and 210, preferably between 195 and 205, most preferred at 199 pmol/l. The optimum threshold to for the group BMI<30 was 231 pmol/l. Naturally, the absolute values of thresholds vary, depending on the assay and the calibration method used. The thresholds mentioned herein were estimated by the same assay and the same calibration that has been used for determining the results in [Clinical Chemistry 50, No. 1, 2004, pages 234-236].

Surprisingly, it has been found that in the method according to the present invention the optimum threshold for patients with a BMI>30 is lower than for patients with a BMI<30. Thus, subject-matter of the present invention is in particular an in vitro method according to the present invention, wherein the underlying threshold for patients with a BMI>30 is lower than for patients with a BMI<30.

The intra-assay variation coefficient of the assay, defined as variation coefficient, which results for a given measurement value from a 10-fold determination in one reaction batch, is preferably at most 10% for all measurement values. It is disadvantageous to exceed this value, as this may lead to erroneous attributions of measurement values in respect to thresholds and may therefore lead to false conclusions.

Therefore, the in vitro methods according to the present invention may be performed with patients having a BMI below 30 kg/m² and with patients having a BMI above or equal to 30 kg/m². Threshold values of from 190 to 260 pmol/l, preferably of from 195 to 240 pmol/l, are suitable for the methods of the present invention independent of the BMI of the patient. However, in preferred embodiments of the invention, the threshold values for patients with BMI equal or greater than 30 kg/m² is chosen such that it is in the range between 190 and 210, preferably between 195 and 205, most preferred at 199 pmol/l. The optimum threshold for the group BMI<30 is 231 pmol/l.

In particular, the sample provided by a patient may be plasma, serum, blood or urine.

According to the invention, the antibodies may be monoclonal as well as polyclonal antibodies. Thus, at least one antibody is a monoclonal or polyclonal antibody.

Preferred are polyclonal antibodies, in particular affinity purified polyclonal antibodies.

The method according to the present invention is particularly preferred wherein the mid-regional area of amino-terminal proANP, spanning amino acid 50 to amino acid 90, is used for the determination of amino-terminal proANP or partial peptides thereof in a sample.

In another particularly preferred embodiment amino-terminal proANP or partial peptides thereof in a sample are determined with a sandwich immunoassay applying two antibodies. In particular, this is preferred if amino-terminal proANP or partial peptides thereof are determined by the use of two antibodies, which specifically bind to different partial sequences of N-terminal proANP.

It is particularly preferred that one of the antibodies is obtained by immunizing an animal with an antigen containing a synthetic peptide sequence comprising amino acids 53-72 of proANP, and the other antibody is obtained by immunizing an animal with an antigen containing a synthetic peptide sequence comprising amino acids 73-90 of proANP. In another embodiment the synthetic peptide sequence comprising amino acids 53-72 of proANP has an additional N-terminal cysteine group. In another preferred embodiment the other antibody is obtained by immunizing an animal with an antigen containing a synthetic peptide sequence comprising amino acids 72-90 or 73-83 of proANP together with an additional N-terminal cystein group. The antibodies obtained by the use of said synthetic peptides, together representing a complete mid-regional part of the proANP sequence, therefore only recognize binding areas in the range of amino acids 53-83 of NT-proANP, and can detect said range completely in form of polyclonal antibodies.

In a preferred embodiment of the in vitro method according the invention, one of the antibodies is labelled and the second is bound to or may be bound selectively to a solid phase.

In a particularly preferred embodiment of the assay, one of the antibodies is labeled while the other is either bound to a solid phase or can be bound selectively to a solid phase. In a preferred embodiment the method is executed as heterogeneous sandwich immunoassay, wherein one of the antibodies is immobilized on an arbitrarily chosen solid phase, for example, the walls of coated test tubes (e.g. polystyrol test tubes; coated tubes; CT) or microtiter plates, for example composed of polystyrol, or to particles, such as for instance magnetic particles, whereby the other antibody has a group resembling a detectable label or enabling for selective attachment to a label, and which serves the detection of the formed sandwich structures. A temporarily delayed or subsequent immobilization using suitable solid phases is also possible.

The method according to the present invention can furthermore be embodied as a homogeneous method, wherein the sandwich complexes formed by the antibody/antibodies and the proANP or proANP partial peptide which is to be detected remains suspended in the liquid phase. In this case it is preferred, that when two antibodies are used, both antibodies are labeled with parts of a detection system, which leads to generation of a signal or triggering of a signal if both antibodies are integrated into a single sandwich. Such techniques are to be embodied in particular as fluorescence enhancing or fluorescence quenching detection methods. A particularly preferred embodiment relates to the use of detection reagents which are to be used pair-wise, such as for example the ones which are described in U.S. Pat. No. 4,882,733, EP-B10 180 492 or EP-B10 539 477 and the prior art cited therein. In this way, measurements in which only reaction products comprising both labeling components in a single immuno-complex directly in the reaction mixture are detected, become possible. For example, such technologies are offered under the brand names TRACE® (Time Resolved Amplified Cryptate Emission) or KRYPTOR®, implementing the teachings of the above-cited applications.

In principle, all labeling techniques which can be applied in assays of said type can be used, such as labeling with radio-isotopes, enzymes, fluorescence-, chemoluminescence- or bioluminescence labels and directly optically detectable colour labels, such as gold atoms and dye particles, which are used in particular in Point-of-Care (POC) or rapid tests. In the case of heterogeneous sandwich immunoassays, both antibodies may exhibit parts of the detection system according to the type described herein in the context of homogenous assays.

In a preferred alternative both the first and the second antibody are dispersed in the liquid reaction medium, whereby a first labeling component which is part of a labeling system based on fluorescence- or chemoluminescence quenching or enhancement is bound to the first antibody, and whereby the second labeling component of this labeling system is bound to the second antibody, such that after binding of both antibodies to the amino-terminal proANP which is to be detected, a detectable signal is generated which enables for a detection of the sandwich complexes formed in the measuring solution. One embodiment of this alternative comprises the labeling system rare earth kryptates or chelates in combination with a fluorescence- or cheminoluminescence-dye. In particular preferred embodiment the labelling system comprises a rare earth kryptate in combination with a fluorescence or chemiluminescence dye.

In a further preferred embodiment, the detection is carried out with a competitive immunoassay. In a particularly preferred embodiment a radioimmunoassay is used.

The method according to the present invention can be conducted in combination with other markers and/or methods. This means that the measurement methods according to the present invention can be conducted particularly advantageously as multi-parameter diagnostic. Hereby, at least one further marker, preferably chosen from the group of inflammatory markers, cardiovascular markers, or ischemic markers is determined additionally.

In a preferred embodiment of the method the inflammatory marker is selected from the group comprising C-reactive protein (CRP), cytokines, such as TNF-alpha, interleukins, such as IL-6, procalcitonin (1-116 or partial peptides thereof) and adhesion molecules, such as VCAM or ICAM.

In a preferred embodiment of the method the cardiovascular marker is selected from the group comprising at least one marker of the group myeloperoxidase, complete peptides or partial peptides of: proBNP, pro-Endothelin-1, proAdrenomedullin, ProVaspressin, pro-Gastrin-Releasing Peptide (pro-GRP), pro-Leptin, pro-Neuropeptide-Y, pro-Somatostatin, pro-Neuropeptide-YY, pro-Opionmelanocortin.

In a preferred embodiment of the method the ischemic marker is selected from the group comprising at least one marker of the group Troponin I or T, CK-MB, myoglobin.

Hereby the markers can be determined in parallel or simultaneously in the method according to the present invention. In the aforementioned multi-parameter determinations it can be envisaged that the measurement results for a number of parameters are evaluated simultaneously or in parallel and for example with the aid of a computer program using diagnostically significant correlations of parameters.

In the method according to the present invention an echocardiography or an electrocardiogram can be recorded as an additional method.

As outlined above the cardiac disease of the patient may be but is not limited to chronic heart failure, acute heart failure, acute coronary syndrome or myocardial infarction.

As discussed above, it is therefore within the scope of the present invention to develop the methods according to the present invention as a rapid test-assay.

Hereby, the sample provided by a patient having a cardiac disease or being suspected of developing or having a cardiac disease and optionally having a BMI of equal or greater than 30 kg/m$^2$ is:
  applied to the sample application zone of a rapid test system,
  contacted with at least one antibody which specifically binds to partial sequences of amino-terminal proANP in the reaction zone, and whereby
  amino-terminal proANP or partial peptides derived thereof to which the antibody/antibodies are bound are detected in the detection zone.
Preferably, the rapid test system may be a microfluidic test system.

In a further preferred embodiment, the rapid test system may be a lateral flow test device. This rapid test system may be a solid phase lateral flow test device.

The method according to the present invention can be executed in a rapid test system based on immuno-migration and/or chromatography.

Thus, a further embodiment of the present invention is a rapid test system for the implementation of the method according to the present invention in all embodiments described herein for the determination of amino proANP or partial peptides thereof in the sample of a patient with a cardiac disease or being suspected of developing or having a cardiac disease and optionally having a BMI of equal or greater than 30 kg/m$^2$, wherein at least one antibody, which specifically binds to partial sequences of amino-terminal proANP is used. Preferably, the partial sequences are at least 12 amino acids in length. More preferably the partial sequences are from 50 to 98 amino acids in length.

Thus, further subject matter of the invention is also the use of at least one antibody specifically binding to partial sequences of amino-terminal proANP for medicinal diagnosis, prognosis and therapy follow-up for patients being suspected of having or developing a cardiac disease and optionally having a BMI of equal or greater than 30 kg/m$^2$.

In the following the invention is explained in more detail by the description of the obtained results of the determination of NT-proANP and NP-proBNP in biological samples of patients.

EXAMPLES

Example 1

An assay as described in [Morgenthaler, N. G. et al., Clin Chem, 2004. 50(1): p. 234-6]] was used for the measurement of amino-terminal proANP. NT-proBNP was determined using the commercially available test by Roche according to the manual (Elecsys).

Both markers were determined in plasma samples of patients with chronic heart failure. In particular the sub-group of patients (n=144) with a Body Mass Index >=30 kg/m$^2$ was further investigated. Of these 144 patients, 26 patients died in the course of 24 months due to cardiovascular events. For evaluation of the prognostic efficiency of both markers, data were analyzed by Cox-regression (StatView 5.0 software for windows; Abacus Concepts, Berkley, Calif.). The median of the values for NT-proBNP (in pg/ml) was 5 times greater than for amino-terminal proANP (in pmol/l). Therefore, the risk ratio for NT-proBNP in comparison to MR-proANP was calculated for a 5 times bigger increase in concentration in the Cox-analysis.

Results of the Univariant Cox Proportional Hazard Analysis:

| MarkerChiSquare | RiskRatio (95% CI) | p |
|---|---|---|
| NT-proANP(100 pmol/l increase) | 14.414 1.503(1.217-1.855) | <0.0001 |
| NT-proBNP(500 pg/ml increase) | 0.662 1.024(0.963-1.094) | 0.416 |

Independent of the fact that no significant result was obtained for NT-proBNP (p=0.416), the RiskRatio of 1.503 for NT-proANP in comparison to NT-proBNP (1.024) clearly shows the advantage in the sub-group of patients with a BMI>=30. A risk ratio of 1.000 indicates that the risk of death per concentration unit does not increase. For NT-proANP a risk ratio of 1.503 therefore means that the risk of death per concentration unit (here 100 pmol/l) increases by 50.3%. In comparison to NT-proBNP this is a 21-fold greater increase of the risk.

Result of the Mulitvariant Cox Proportional Hazard Analysis:

| MarkerChiSquare | RiskRatio (95% CI) | p |
|---|---|---|
| LN NT-proANP | 7.198 2.776(1.317-5.854) | 0.007 |
| LN NT-proBNP | 0.005 0.985(0.644-1.506) | 0.943 |

Again, the result demonstrates the advantage of NT-proANP as it persists as independent predictor for death in the sub-group of patients with the BMI >=30 in a model with NT-proBNP (p=0.007). In contrast thereto, NT-proBNP is not an independent predictor.

Also in the ROC analysis NT-proANP was superior to NT-proBNP (AUC=0.61) for the mortality prognosis of the sub-group of patients with the BMI >=30 with an AUC of 0.66. The optimum threshold of NT-proANP for the prognosis ways 199 pmol/1.

Example 2

Study Population

We prospectively enrolled consecutive patients presenting to the ED. To be eligible for the study, a patient had to have dyspnea as the most prominent symptom. Patients under 18 years of age, patients on hemodialysis and trauma patients were excluded. The study was carried out according to the principles of the Declaration of Helsinki and approved by the local ethics committee. Written informed consent was obtained from all participating patients.

Clinical Evaluation of Patients

Patients underwent an initial clinical assessment that included clinical history, physical examination, ECG, pulse oximetry, blood tests including arterial blood gas analysis (when indicated) and chest x-ray. Echocardiography and pulmonary function tests were strongly recommended in the ED on an outpatient basis or in the hospital if the patient was admitted. For each patient enrolled in the study, ED physicians assessed the probability that the patient had HF (by assigning a value of 0 to 100 percent clinical certainty) as the cause of his or her dyspnea including all available information of the physical examination, ECG, chest x-ray and blood tests including BNP.

Reference ("Gold") Standard Definition of Heart Failure

To determine the actual diagnosis, two independent cardiologists reviewed all medical records pertaining to the patient and independently classified the diagnosis as dyspnea due to HF or dyspnea due to another cause than HF. Both cardiologists had access to the ED charts and any additional information that became available during or after the evaluation in the ED. This information included the BNP levels, chest x-ray, medical history that was not available to the ED physicians, results of subsequent tests such as echocardiography, radionuclide imaging, or left ventriculography, performed at the time of cardiac catheterization, pulmonary function test, CT scan, compression ultrasound for the assessment of pulmonary embolism, right heart catheterization, the hospital course for patients admitted to the hospital, the response to therapy, autopsy data in deceased patients and information about clinical events or readmissions during 90-day follow up. The BNP level was considered as a quantitative marker of HF and therefore interpreted as a continuous variable to make best use of the information provided by this test. The higher the BNP level, the higher the probability of HF being present and to be the cause of dyspnea. Absolute BNP values were adjusted for the presence of kidney disease and obesity to maximize diagnostic accuracy (Mueller, C. et al., Swiss Med Wkly, 2007. 137(1-2): p. 4-12.).

Measurement of Natriuretic Peptides

During initial evaluation, a blood sample was collected into tubes containing potassium EDTA. The MR-proANP and NT-proBNP were analyzed from plasma samples immediately frozen at −80° C. until analysis. Detection of MR-proANP was performed using a sandwich immunoassay (MR-proANP LIA, B.R.A.H.M.S, Hennigsdorf/Berlin, Germany) as described in detail elsewhere (Morgenthaler, N. G., et al., Gin Chem, 2004. 50(1): p. 234-6.). Median MR-proANP in 325 healthy individuals in previous investigations was 45 pmol/l (95% confidence interval (CI) 43 to 49 pmol/l) (Morgenthaler, N. G., et al., Clin Chem, 2004. 50(1): p. 234-6.). The NT-proBNP levels were determined by a quantitative electrochemiluminescence immunoassay (Elecsys proBNP, Roche Diagnostics AG, Zug, Switzerland). BNP was measured by a microparticle enzyme immunoassay (Ax-Sym, Abbott Laboratories, IL, USA).

Statistical Analysis

Univariate data on demographic and clinical features were compared between patients with dyspnea due to HF and patients with dyspnea not due to HF by the non-parametric Mann-Whitney U test or Fisher's exact test as appropriate. MR-proANP and NT-proBNP were considered as continuous variables and were log-transformed to achieve normality. The primary objective was to compare the accuracy of MR-proANP with that of NT-proBNP. As BNP levels were available for the reference ("Gold") standard diagnosis of HF, the comparison of the MR-proANP with BNP was considered biased in favor of BNP and therefore BNP was not included in the ROC analysis. The secondary objective was to investigate, whether the addition of MR-proANP to clinical judgment in the ED, including chest x-ray and BNP information, would further increase diagnostic accuracy. To determine the diagnostic accuracy of MR-proANP and NT-proBNP for HF, receivers operating characteristic (ROC) curves were analyzed and areas under the curve (AUCs) were calculated for both markers. AUCs were compared according to the method by Hanley and McNeil (Hanley, J. A. et al., Radiology, 1983. 148(3): p. 839-43.). The optimal cut-off-point was arrived by selecting the point on the ROC curve that maximized both sensitivity and specificity. The optimum cut point for ED clinical certainty of HF was chosen at .gtoreq.80%, a cut point providing reasonable and actionable certainty McCullough, P. A., et al., Circulation, 2002. 106(4): p. 416-22. The diagnostic accuracies of both assays at optimal cut-off concentrations as determined by ROC analysis were compared by the McNemar test (comparison of discordant pairs of false biochemical classifications). To determine odds ratios for the detection of HF with respect to MR-proANP and NT-proBNP thresholds of highest diagnostic accuracy, logistic regression analysis was performed unadjusted and adjusted for significant covariates (age, prior CHF, prior myocardial infarction, estimated glomerular filtration rate, hemoglobin, pulmonary rales, peripheral edema and jugular venous distension). Spearman's coefficient of rank correlation was used to assess the relation of MR-proANP and NT-proBNP concentrations in the study population. Body mass index (BMI) was calculated using the conventional formula of weight in kilograms divided by the square of height in meters. Normal weight was defined as a BMI<25 kg/m², overweight as a BMI between 25 kg/m² and 29.9 kg/m² and Obesity as a BMI of 30 kg/m² or greater, according to the definition of the World Health Organization. Glomerular filtration rate was calculated using the Modification of Diet in Renal Disease (MDRD) formula (Stevens, L. A. et al., N Engl Med, 2006. 354(23): p. 2473-83.). Data were statistically analyzed with SPSS15.0 software (SPSS Inc, Chicago, Ill., USA) and the MedCalc 9.3.9.0 package (MedCalc Software, Mariakerke, Belgium). All probabilities were two tailed and p<0.05 was regarded as significant.

Results

Figure 1:
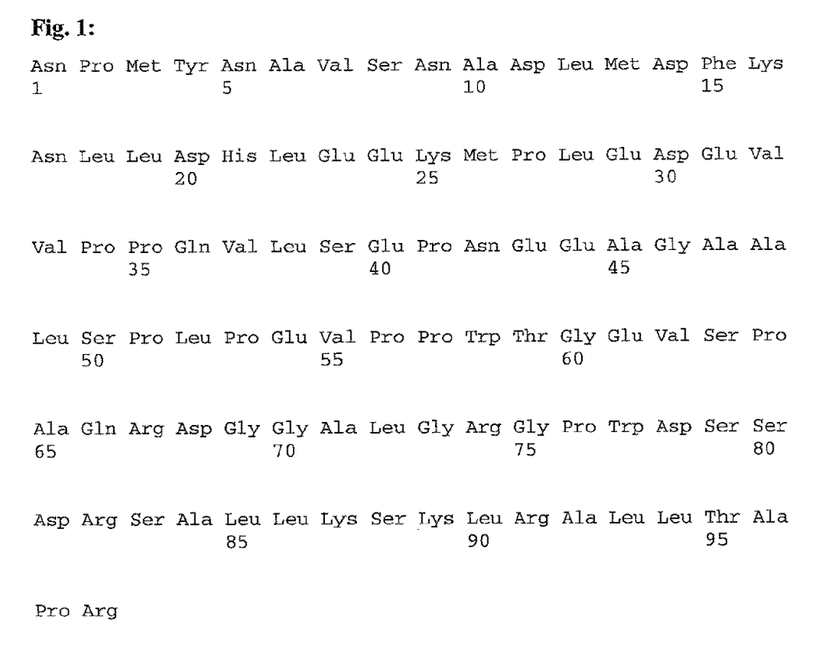
FIG. 1: shows the sequence of NT-proANP.
Figure 2:
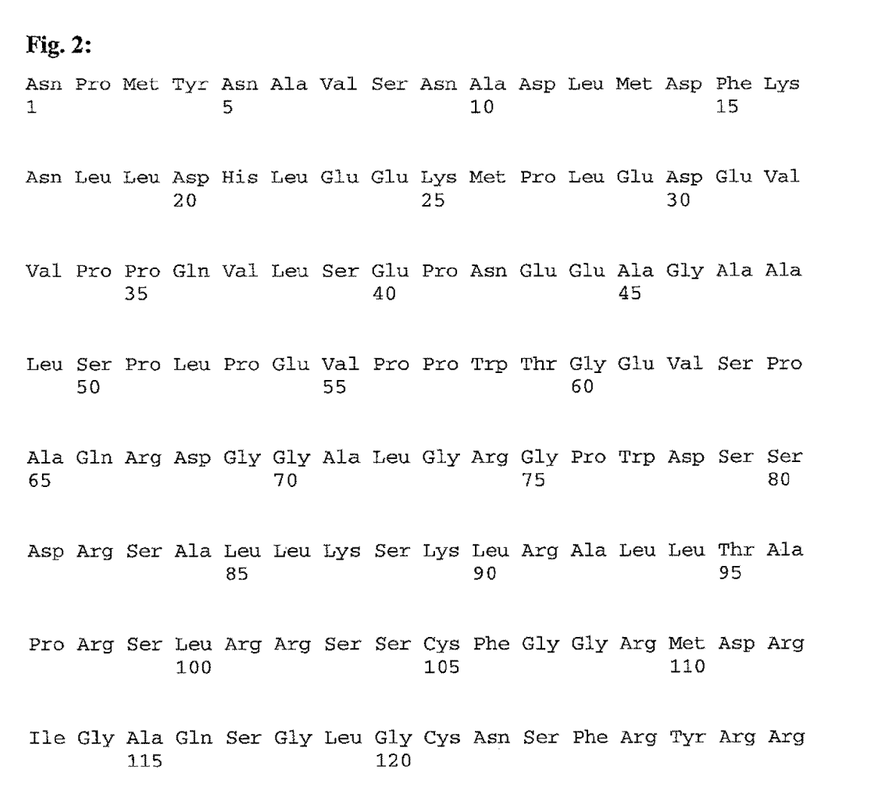
FIG. 2: shows the sequence of proANP. Table illustrating the baseline characteristics of 287 patients.
Figure 3:
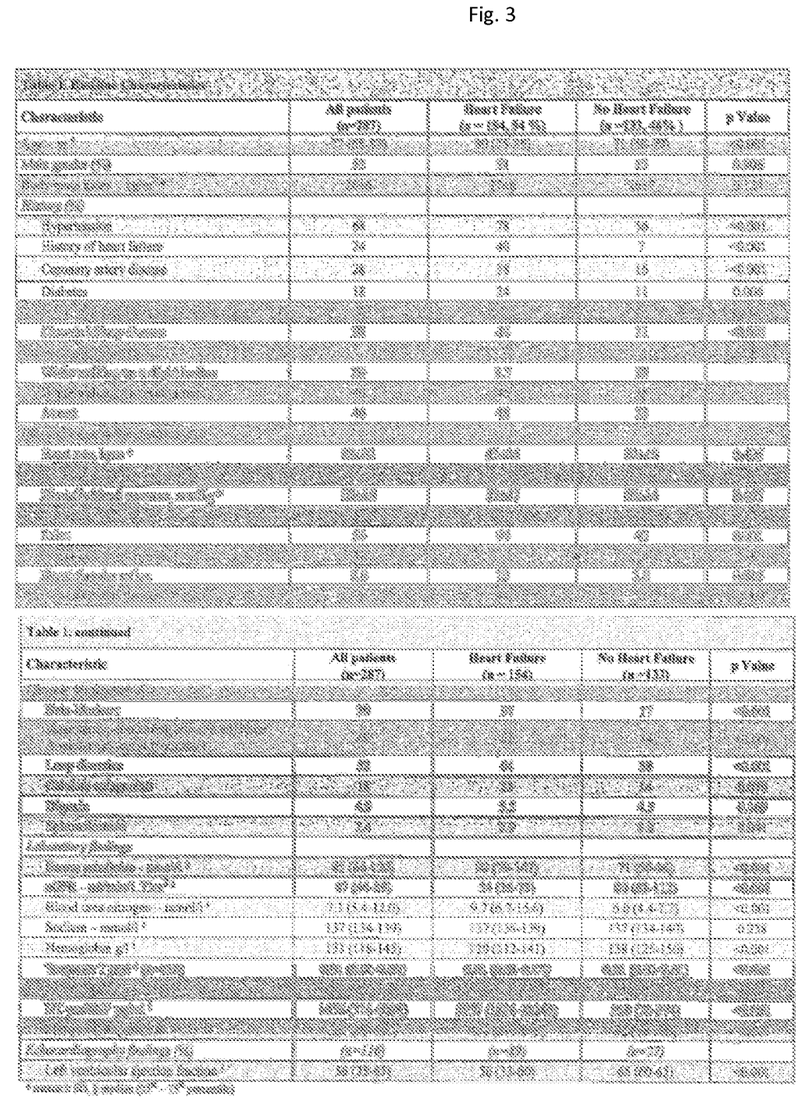
FIG. 3: Table illustrating the baseline characteristics of 287 patients; eGRF=estimated glomerular filtration rate; MR-proANP=midregional pro-atrial natriuretic peptide; NT-proBNP=N-terminal pro-B-type natriuretic peptide.

A total of 287 patients were enrolled in this study (FIG. 3). The median age was 77 years. There were 149 men (52%) and 138 women (48%). Arterial hypertension was present in 68% of the patients, 28% had coronary heart disease, and 34% had chronic obstructive pulmonary disease. Diuretics (52%) were the most common prescribed chronic medications, followed by ACE-inhibitors or AT-II-receptor-blockers (49%) and beta-blockers (39%). On examination, 54% of patients had rales in the lower lung fields, 42% had lower extremity edema and 28% had jugular venous distension.

The adjudicated gold standard diagnosis was HF in 154 (54%) patients, chronic obstructive pulmonary disease in 71 (25%) patients, pneumonia in 33 (11%) patients, malignancy in 10 (3%) patients, pulmonary embolism in 8 (3%) patients, hyperventilation in 7 (2%) patients and other causes such as interstitial lung disease, asthma or bronchitis in 14 (5%) patients. There were several patients with two main reasons for dyspnea such as exacerbation of chronic obstructive pulmonary disease and pneumonia.

Figure 4:
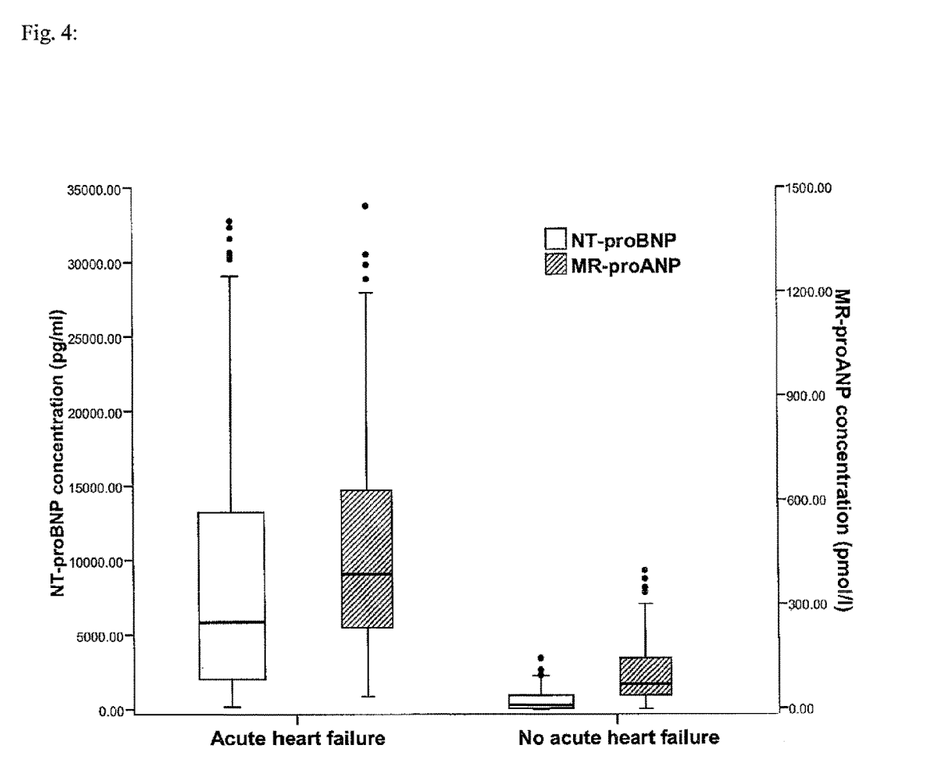
FIG. 4: Box plots showing levels of NT-proBNP and MR-proANP for patients with dyspnea caused by heart failure (n=154) and patients with dyspnea attributable to other causes (n=133); all p<0.001.
Figure 5:
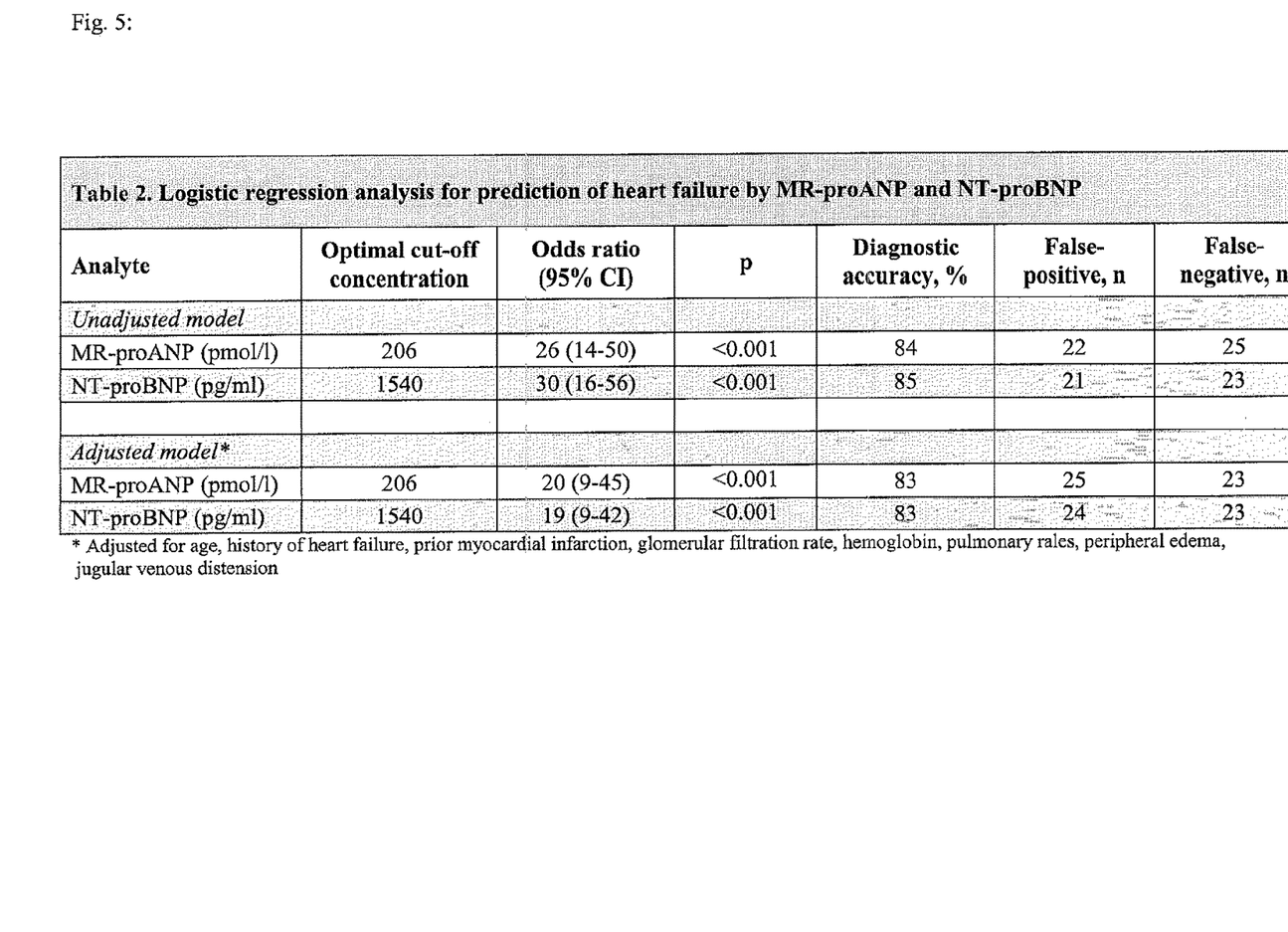
FIG. 5: Table illustrating logistic regression analysis for prediction of heart failure by MR-proANP and NT-proBNP; MR-proANP=midregional pro-atrial natriuretic peptide; NT-proBNP=N-terminal pro-B-type natriuretic peptide. Table illustrating logistic regression analysis for prediction of heart failure by MR-proANP and NT-proBNP.
Figure 6:
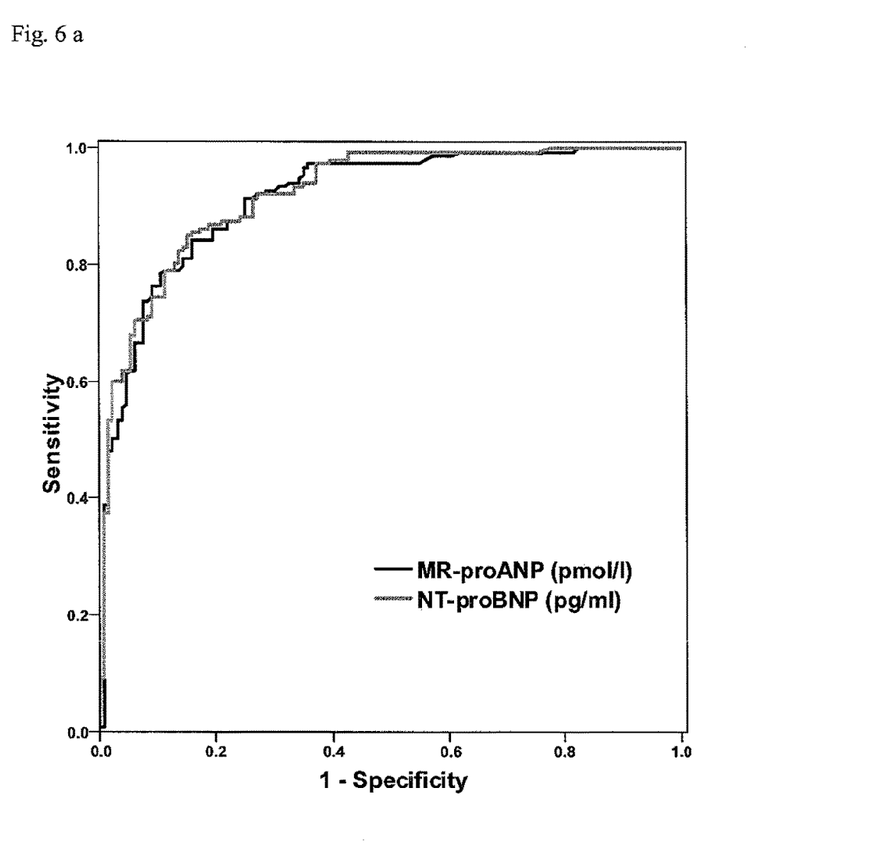
FIG. 6a: Receiver operating characteristic (ROC) curve for the accuracy of NT-proBNP and MR-proANP to diagnose heart failure in patients with dyspnea. Area under the curve (AUC): for NT-proBNP=0.92; for MR-proANP=0.92 (p=0.791 for comparison).
FIG. 6b: Receiver operating characteristic (ROC) curve for emergency department (ED)-probability, MR-proANP, and both in the detection of heart failure. (Area under the curve (AUC): for MR-proANP=0.92; for ED-probability=0.90; for combination=0.96; p=0.016 for comparison of ED-probability and combination of ED-probability with MR-proANP).

The levels of MR-proANP and NT-proBNP in patients with and without an adjudicated gold standard diagnosis of HF are shown in FIG. 4. The median MR-proANP concentration of those patients with HF (400 pmol/L, IQR 246-642 pmol/l) was significantly higher than of those without HF (92 pmol/L, IQR 92-173 pmol/l; p<0.001 for difference). The median NT-proBNP concentration in patients with HF was 5757 pg/ml (IQR 1924-13243 pg/ml) vs. 300 pg/ml (IQR 76-974 pg/ml) in patients without HF (p<0.001 for difference). Spearman's coefficient of rank correlation was 0.899 between MR-proANP and NT-proBNP (p<0.001). The AUC of MR-proANP was 0.92 (95% CI 0.88 to 0.95) for the diagnosis of HF, identical to the AUC of NT-proBNP with 0.92 (95% CI 0.89 to 0.95; p=0.791; FIG. 6a). On the basis of the ROC analysis, the optimal diagnostic cut-off-value for MR-proANP and NT-proBNP to reach the highest diagnostic accuracy was 206 pmol/l and 1540 pg/ml, respectively. At this cut-off, accuracy, sensitivity and specificity for MR-proANP were all 84%. Logistic regression analysis confirmed MR-proANP as a powerful predictor of HF in both, univariate and multivariate analyses (FIG. 5).

Figure 7:
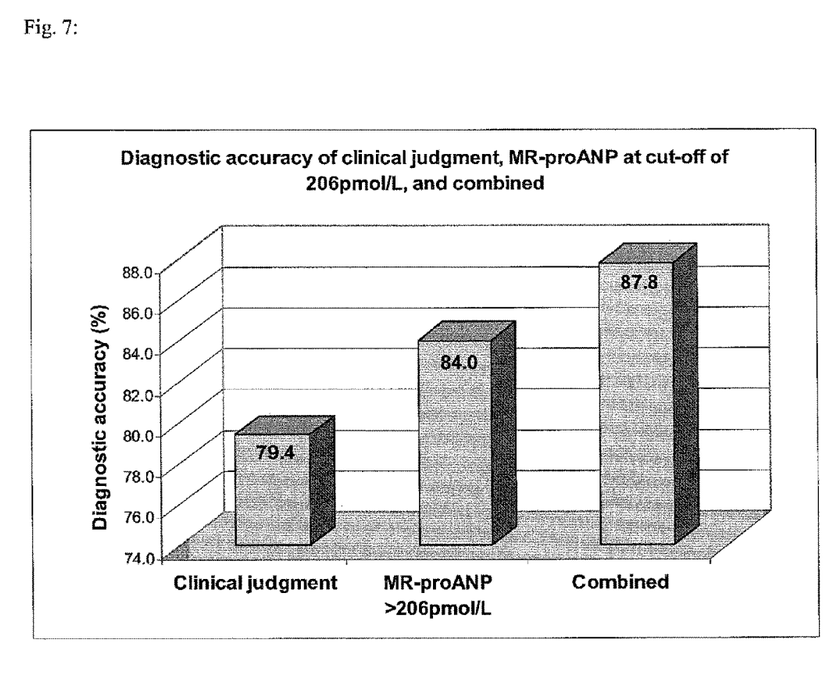
FIG. 7: Diagnostic accuracy of clinical judgment (high emergency department probability for heart failure), MR-proANP using a cut-off level of 206 pmol/L, and both combined in the detection of heart failure (p<0.001).

The AUC for the combination of ED-probability with MR-proANP was significantly higher than for ED-probability alone (p=0.016, FIG. 6b). The diagnostic accuracy for clinical judgment with high ED probability of HF (80% to 100% clinical certainty) was 79.4%. Therefore, as an overall measure of diagnostic value, MR-proANP levels>206 pmol/L added to ED-probability would have increased the diagnostic accuracy considerably to 87.8% (p<0.001, FIG. 7). Overall, MR-proANP at a cut-off-value of 206 pmol/L and ED-probability 80% certainty were relatively independent indicators, as reflected by a Cohens Kappa value of 0.47 (p<0.001).

Figure 8:
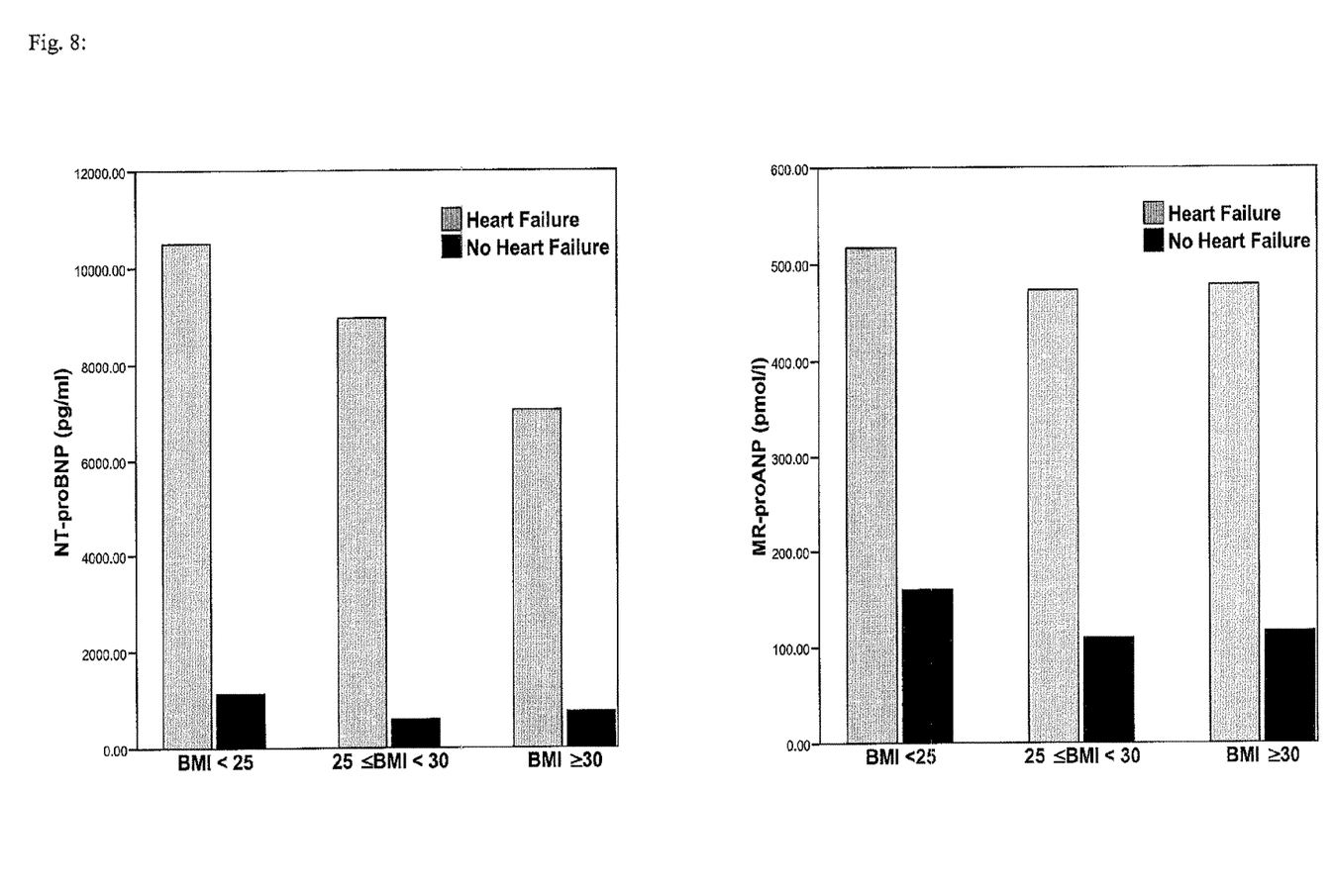
FIG. 8: Mean NT-proBNP and MR-proANP levels in patients with and without heart failure, grouped by body mass index (BMI).

As shown in FIG. 8, MR-proANP and NT-proBNP differed regarding their association with BMI. In patients with HF, mean MR-proANP levels were not different in overweight and obese patients compared with individuals with normal BMI (p=0.346 for both), whereas NT-proBNP levels were lower in overweight and obese patients than in normal weight patients (p=0.025 for both).

The invention claimed is:

1. An in vitro method for medical diagnosis, prognosis and therapy follow-up for a patient having a cardiac disease or suspected of developing or having a cardiac disease,
   detecting and quantitating in a sample from said patient at least one marker comprising the midregional area of the amino-terminal portion of pro-atrial natriuretic peptide (proANP [SEQ ID NO:2]) ("NT-pro-ANP", consisting of amino acids 1-98 of SEQ ID NO:2), said midregional area of pro-ANP (MR-proANP) spanning amino acids 50-90 of SEQ ID NO:2, or partial peptides of NT-proANP, collectively NT-proANP analytes, said analytes having from 12 to 98 amino acids,
   wherein said detection and quantitation comprises
      (i) contacting said sample with at least two different antibodies that specifically bind to partial sequences within MR-proANP, and
      (ii) detecting the amount of bound antibody;
   whereby when the amount of bound antibody corresponds to a level of pro-ANP analyte that is higher than a cut-off value of from 190 to 260 pmol/L, as determined in a sample of plasma, and which level is independent of the BMI of the patient, the level of pro-ANP analyte indicates that the patient has or is developing a cardiac disease,
   wherein attribution of this indication to the patient's clinical picture is used for diagnosis, prognosis or therapeutic follow up of said patient.

2. The in vitro method of claim 1, wherein the cardiac disease is selected from a group comprising chronic heart failure, acute heart failure, acute coronary syndrome and myocardial infarct.

3. The in vitro method of claim 1, wherein said method is a method for medical diagnosis.

4. The in vitro method of claim 1, wherein the patient exhibits symptoms of dyspnea and is therefore suspected of having heart failure.

5. The in vitro method of claim 1, wherein the patient or the patient group has a BMI of equal or greater than 30 kg/m$^2$ and the sample is provided by a patient having a BMI of equal or greater than 30 kg/m$^2$.

6. The in vitro method of claim 5 wherein the method is a method of prognosis.

7. The in vitro method of claim 5, wherein the disease is chronic heart failure.

8. The in vitro method of claim 1, wherein the sample is plasma, serum, blood, or urine.

9. The in vitro method of claim 1, wherein the method is carried out in combination with at least one other marker and/or method.

10. The in vitro method of claim 1, wherein at least one other marker is determined in a sample from the patient, and wherein the marker is selected from an inflammatory marker, a cardiovascular marker, or an ischemic marker.

11. The in vitro method of claim 10, wherein the inflammatory marker is C-reactive protein (CRP), a cytokine, an interleukin, procalcitonin 1-116 or a peptide fragment thereof having from 12 to 116 amino acids, or an adhesion molecule.

12. The in vitro method of claim 10, wherein the cardiovascular marker is myeloperoxidase, the entire Pro-B-type natriuretic peptide (proBNP) or peptide fragments of proBNP of at least 12 amino acid residues in length, pro-endothelin-1, pro-adrenomedullin, pro-Vasopressin, pro-gastrin-releasing peptide (proGRP), pro-Leptin, pro-neuropeptide-Y, pro-somatostatin, pro-neuropeptide-YY, or pro-opiomelanocortin.

13. The in vitro method of claim 10, wherein the ischemic marker is selected from a group comprising troponin I or T, CK-MB, myoglobin.

14. The in vitro method of claim 1, wherein the method is conducted as rapid test assay.

15. A method of claim 12, wherein the protein fragments are BNP or N-terminal pro-BNP (NT-proBNP).

16. A method of claim 11, wherein if the inflammatory marker is a cytokine, the cytokine is TNF-alpha.

17. A method of claim 11, wherein if the inflammatory marker is an interleukin, the interleukin is IL-6.

18. A method of claim 11, wherein if the inflammatory marker is a procalcitonin peptide fragment, it has from 100-116 amino acids.

19. A method of claim 11, wherein if the inflammatory marker is an adhesion molecule, the adhesion molecule is VCAM or ICAM.

* * * * *